(12) United States Patent
Pizolato

(10) Patent No.: US 10,117,676 B2
(45) Date of Patent: Nov. 6, 2018

(54) METHOD OF EMBRYO TRANSFER THAT ELIMINATES TRANSFERRED AIR WHILE HORMONALLY INDUCING IMPLANTATION AND APPARATUS

(71) Applicant: Incintas Therapeutics, Inc., Atglen, PA (US)

(72) Inventor: Jesse Albert Pizolato, Atgen, PA (US)

(73) Assignee: Incintas Therapeutics, Inc., Atglen, PA (US)

( * ) Notice: Subject to any disclaimer, the term of this patent is extended or adjusted under 35 U.S.C. 154(b) by 267 days.

(21) Appl. No.: 14/797,411

(22) Filed: Jul. 13, 2015

(65) Prior Publication Data

US 2015/0313639 A1 Nov. 5, 2015

Related U.S. Application Data

(63) Continuation-in-part of application No. 12/348,571, filed on Jan. 5, 2009, now Pat. No. 9,107,696.

(Continued)

(51) Int. Cl.
*A61B 17/435* (2006.01)
*A61B 17/00* (2006.01)
(Continued)

(52) U.S. Cl.
CPC ...... *A61B 17/435* (2013.01); *A61B 17/00234* (2013.01); *A61M 25/00* (2013.01); *A61M 25/0067* (2013.01); *A61B 2017/00292* (2013.01); *A61B 2090/063* (2016.02); *A61B 2090/0807* (2016.02); *A61M 2025/0008* (2013.01); *A61M 2210/1433* (2013.01)

(58) Field of Classification Search
CPC .... A61B 17/435; A61M 2210/1433–2210/145
See application file for complete search history.

(56) References Cited

U.S. PATENT DOCUMENTS 4,863,423 A 9/1989 Wallace
5,084,277 A 1/1992 Greco et al.
(Continued)

FOREIGN PATENT DOCUMENTS

WO WO02067772 A2 9/2002

OTHER PUBLICATIONS

Eytan, Osnat et al., A glance into the uterus during in vitro simulation of embryo transfer, 2004, pp. 1-8, European Society of Human Reproduction and Embryology, 2004, Tel-Aviv, Isreal.
(Continued)

*Primary Examiner* — Thaddeus Cox
(74) *Attorney, Agent, or Firm* — Joseph F. Aceto, Esq.

(57) ABSTRACT

A method of embryo transfer ("ET") that improves fertility rates by eliminating transferred air during the procedure is provided. Also provided is a method for hormonally enhancing the uterine wall of a patient either prior to or during the time of ET. Quantitative administration of transfer solutions is accomplished with a modified apparatus that provides for implantation of an embryo into the uterus of a patient. The apparatus comprises an outer sheath and an inner lumen arranged to be slidably disposed within the outer sheath. The inner lumen includes at least one visual marker situated on the exterior surface adjacent its distal end thereof.

9 Claims, 3 Drawing Sheets

Related U.S. Application Data

(60) Provisional application No. 61/188,021, filed on Aug. 6, 2008.

(51) Int. Cl.
  *A61M 25/00* (2006.01)
  *A61B 90/00* (2016.01)

(56) References Cited

U.S. PATENT DOCUMENTS

| | | | |
|---|---|---|---|
| 5,116,619 A | 5/1992 | Greco et al. | |
| 5,472,419 A * | 12/1995 | Bacich | A61B 17/435 600/35 |
| 5,543,150 A | 8/1996 | Bologna et al. | |
| 6,027,443 A | 2/2000 | Nag | |
| 6,165,165 A | 12/2000 | Cecci et al. | |
| 6,527,703 B2 | 3/2003 | Simmet | |
| 6,527,752 B1 | 3/2003 | Bosley, Jr. et al. | |
| 6,544,553 B1 | 4/2003 | Hsia et al. | |
| 6,623,422 B2 | 9/2003 | Kamrava | |
| 6,695,766 B2 | 2/2004 | Moruzzi et al. | |
| 7,175,590 B2 | 2/2007 | Christine et al. | |
| 7,300,664 B1 | 11/2007 | Jossifoff | |
| 7,320,800 B2 | 1/2008 | Jossifoff | |
| 7,393,543 B2 | 7/2008 | Jossifoff | |
| 2003/0208101 A1 | 11/2003 | Cecco | |
| 2006/0058202 A1 | 3/2006 | Zoppetti et al. | |
| 2007/0010013 A1 * | 1/2007 | Bukovsky | C12N 5/0604 435/366 |
| 2010/0036193 A1 * | 2/2010 | Pizolato | A61B 17/435 600/34 |
| 2013/0144114 A1 * | 6/2013 | Simon Valles | G01N 33/5023 600/34 |
| 2015/0342642 A1 * | 12/2015 | Sillender | A61M 25/0017 600/34 |

OTHER PUBLICATIONS

International Search Report re International Application No. PCT/US2009/052698.
Vitrolife Sweden AB, 2003, CCM, Material Safety Data Sheet, RTN No. 00010094, Dec. 12, 2003.
Virolife Sweden AB, 2010, CCM, Material Safety Data Sheet, Dec. 27, 2010.
Virolife Sweden AB, 2009, CCM, Product Insert.
Nelson, "Primary Ovarian Insufficency" N Engl J Med. 2009, 360(6): 606-614.

* cited by examiner

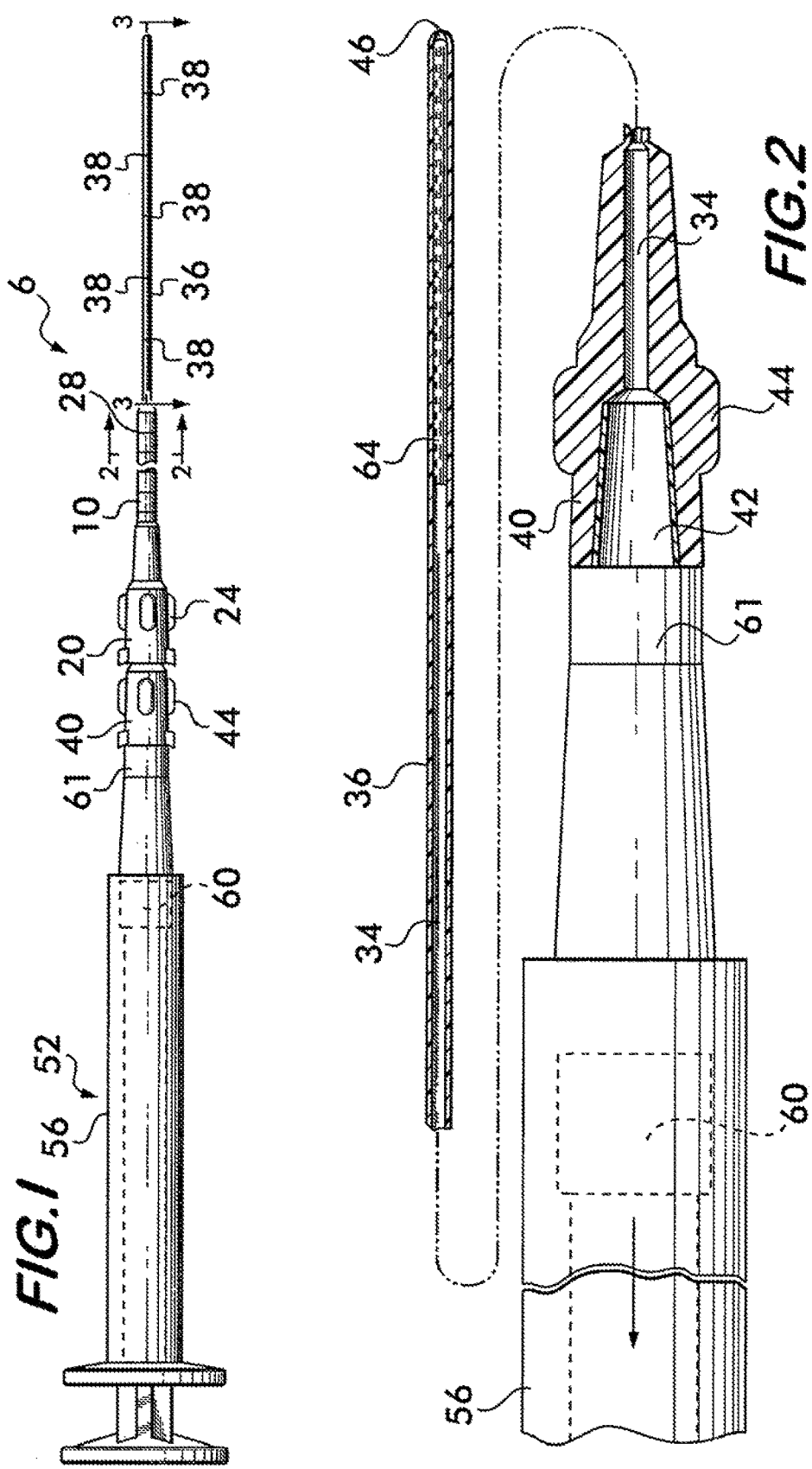

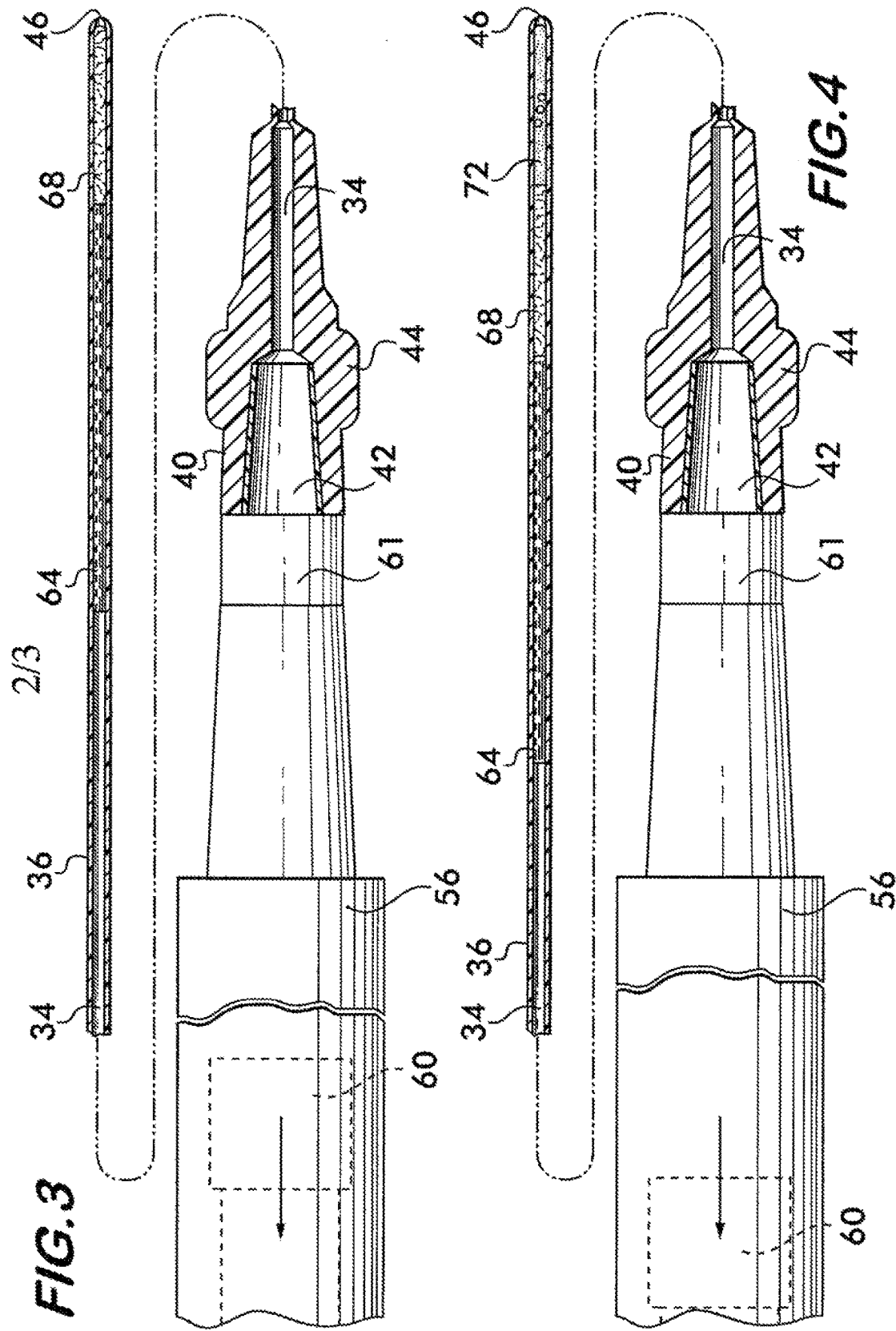

METHOD OF EMBRYO TRANSFER THAT ELIMINATES TRANSFERRED AIR WHILE HORMONALLY INDUCING IMPLANTATION AND APPARATUS

RELATED APPLICATIONS

This application is a continuation-in-part of U.S. application Ser. No. 12/348,571, filed Jan. 5, 2009, which claims the benefit of priority to U.S. Provisional Application No. 61/188,021, filed Aug. 6, 2008, which applications are hereby incorporated by reference in their entireties.

FIELD OF THE INVENTION

This invention relates to a minimally-invasive medical procedure of embryo transfer utilizing a uterine transfer catheter that deposits fertilized eggs into the uterus whereby implantation of an embryo occurs.

BACKGROUND OF THE INVENTION

Human in vitro fertilization (IVF) and embryo transfer (ET) was first successfully performed in 1978 and has since been widely practiced to treat infertile couples who have failed with other conventional methods. The IVF/ET procedure typically involves hormonal stimulation of the female to initially suppress her natural ovulation, and then stimulate development of ovarian follicles with fertility drugs. The mature eggs are harvested from the ovary using a needle and then sorted by maturity and egg quality. Preferred eggs are then mixed with sperm from the male to be fertilized. After some time, the embryo(s) mature and are transferred, along with a volume of fluid, to the uterus using a delivery catheter. The delivery catheter is made of soft plastic material to avoid damage to the endometrium of the uterus. The delivery catheter is guided through the cervix to the uterus by a physician where the loaded embryos within the fluid is deposited, completing the ET.

One method of catheter loading is referred to as "the transfer bubble method" and has been universally accepted by professionals and has been in place over four decades. The catheter is loaded with a series of alternate air and transfer liquid (e.g., saline, P-1 or glycerine) in volumes approximating 3 microliters. Volumes of air separate the transfer liquid to keep the embryos contained within the fluid and also to ease visualization of the components. Upon ejection of the fluids, about 100 microliters of air is also ejected with the quantity of medium and transfer liquid containing the embryos. Generally, there are a total of approximately 6 microliters of fluid and 100 microliters of air deposited at the ejection site in the uterus. These volumes can vary greatly depending on specific hospital protocol and there has been research done to study the effects of varying medium volumes upon pregnancy rates. Some studies demonstrate that a transferred volume of less than 50 microliters is optimal for successful ET whereby other studies show that widely varying transfer volumes of medium have little effect on the outcome of IVF procedures.

Studies also have found that the transferred air within the uterus can sometimes act as a barrier that prohibits movement of the embryos from the site of ejection to the optimal location for implantation within the uterus. This air bubble creates an area of surface tension to which the embryos may adhere and remain positioned, prohibiting interaction of the embryo with the receptive surface of the uterus. Moreover, under the transfer bubble method, latent embryos can attach themselves to the internal walls of the catheter requiring further manipulation of the embryos and thereby decreasing the likelihood of successful ET.

While improvements in the techniques and instrumentation used in this procedure have provided significant increases in pregnancy rates and births, the overall numbers remain fairly low, around 25%. There are several factors that impact on IVF success including the design of the delivery catheter. Ultrasound guided catheters have been included in ET procedures to aid visualization of the tip and facilitate optimized embryo deposition at the prime location within the uterus.

In addition, the high cost of the IVF procedure combined with this low probability of success compels couples to deliver multiple embryos to increase the chance of at least one successful implantation. Often, unwanted multiple births result and jeopardize the health of mother and/or children, which has recently raised questions concerning the medical ethics of such practice. If a higher pregnancy rate could be achieved, the need for multiple embryo delivery would be lessened or possibly eliminated.

With the high cost of IVF and contrastingly low pregnancy rate, what is needed is a method of ET that reduces the quantity of air that is typically transferred to the uterus along with the embryos in medium. The conventional method of catheter loading referred to as "the transfer bubble method" that deposits these relatively large volumes of air has been taught worldwide and universally accepted by professionals in the IVF field. Even as studies demonstrate the difficulties associated with this large transferred air bubble, this method is the only one used. An improved method of ET that eliminates any volume of transferred air will undoubtedly improve the probability of successful embryo implantation and increase pregnancy rates overall.

SUMMARY OF THE INVENTION

A method of embryo transfer ("ET") that improves fertility rates by eliminating transferred air during the procedure is provided. Also provided is a method for hormonally enhancing the uterine wall of a patient at the time of ET.

Direct administration of hormones into the uterus may be achieved by including the hormones in the milieu of solutions utilized during the transfer of one or more embryos into the endometrium during ET. Luteal support is maintained by slow dissolution of the deposited hormones by direct injection into the uterus, as opposed to introducing the hormones systemically. Further direct administration allows for optimizing the delivery time of these hormones in the preparation of the uterus prior to or simultaneously with the delivery of a fertilized egg at the site of implantation.

The present invention embodies a method of targeted intrauterine administration in a timed sequence of events to precisely establish a progesterone dominant uterus that is primed and ready to receive a developing blastocyst for implantation Quantitative administration of the hormonal solutions is accomplished by a modified delivery catheter that comprises an outer sheath having a proximal end and a distal end. An inner lumen is arranged to be slidably disposed within the outer sheath. The inner lumen includes a proximal end, a distal end, and a passageway therethrough. The inner lumen includes at least one visual marker situated on the exterior surface adjacent its distal end thereof to enable accurate volumes of fluid media in which one or more embryos are situated to be drawn into the deliver catheter.

BRIEF DESCRIPTION OF THE DRAWINGS

FIG. 1 is an elevational view of an embodiment of the delivery catheter of the present invention with a syringe shown attached at the proximal end thereof, the syringe including a barrel and a plunger disposed therein.

FIG. 2 is a cross-sectional view taken along line 2-2 of FIG. 1.

FIG. 3 is a cross-sectional view taken along line 3-3 of FIG. 1.

FIG. 4 is a cross-sectional view of a portion of an embodiment of the delivery catheter of the present invention wherein the inner lumen is illustrated as retaining therein a first portion comprised of a wash fluid, a second portion comprised of an oil, and a third portion comprised of one or more embryos disposed within a fluid culture medium.

DETAILED DESCRIPTION OF THE PREFERRED EMBODIMENT

The problems associated with large quantities of transferred air during ET procedures are solved and a technical advance is achieved in an improved delivery catheter for use in an ET procedure and method for loading the delivery catheter that involves replacing the air bubble with a liquid medium, e.g., a separation oil, at the start of the procedure, to improve the rate of fertility.

Figure 5:
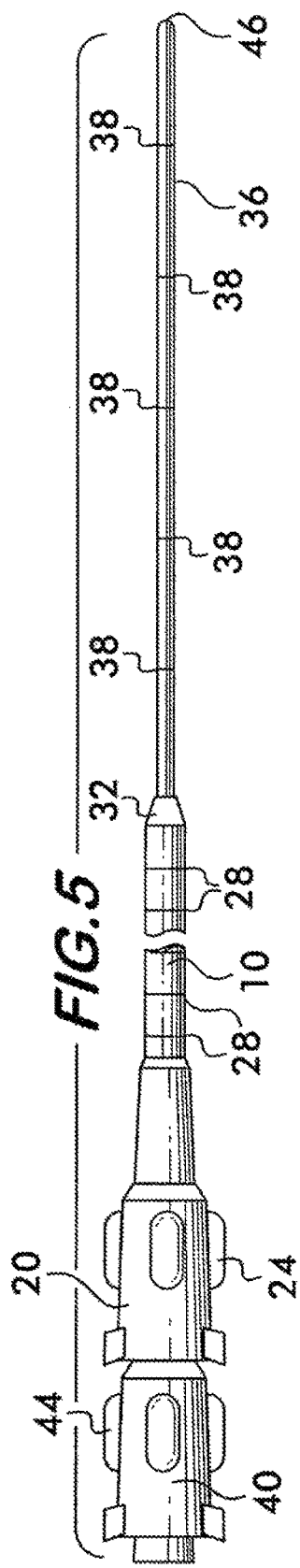
FIG. 5 is a cross-section view of a portion of an embodiment of the delivery catheter of the present invention wherein the inner lumen is illustrated as retaining therein a first portion comprised of a wash fluid, a second portion comprised of an oil, and a third portion comprised of one or more embryos disposed within a fluid culture medium.
Figure 6:
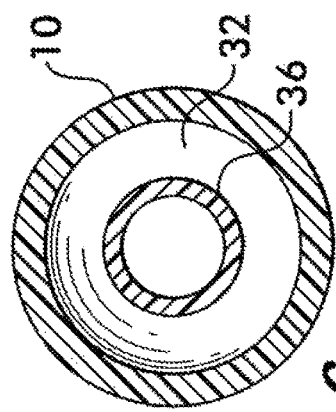
FIG. 6 is a front end view of the delivery catheter of the present invention.

Referring now in detail to the various figures of the drawings wherein like reference characters refer to like parts, there is shown at 6 in FIGS. 1 through 6, an embodiment of the delivery catheter is illustrated as including an outer sheath 10 being in the form of a hollow tube and provided towards its proximal end with a hub 20 provided with a series of axially extending fins 24 to assist in manipulation. As best shown in FIG. 5, the distal end of the outer sheath 10 is provided at intervals of a predetermined distance, e.g., one centimeter, with gradations 28 of any suitable measure, e.g., microliters. The gradations are marked as a plurality of rings about the distal end, and which may be slightly indented into the outer surface thereof. Alternatively, the gradations 28 may be of a distinctive color. As best seen in FIGS. 5 and 6, the remote distal tip 32 of the outer sheath 10 is chamfered for minimal trauma. The outer sheath 10 is formed of any suitable material, and preferably a generally rigid plastic material such as TEFLON®.

The outer sheath 10 is adapted to accommodate therewithin an inner lumen 36 having an external diameter such as to be an easy sliding fit within the outer sheath 10 and an internal passageway 34 having a diameter of a size to readily accommodate an embryo. As best shown in FIGS. 1 and 5, the inner lumen 36 is provided at its proximal end with a hub 40, the hub 40 being provided about its external surface with a plurality of axially extending fins 44 to assist manipulation. The inner lumen 36 is provided with an inner bore 42 (FIG. 2) that is in open communication with the internal passageway 34. The hubs 20 and 40 are adapted such that they interlock in their closed position as shown in FIGS. 1 and 5. The hubs 20 and 40 are provided to enable a physician and/or an embryologist to hold the outer sheath 10 with one hand while using the other hand to slide the inner lumen 36 through the outer sheath 10 during an embryo transfer procedure.

Referring now to FIGS. 1 and 5, the distal end of the inner lumen 36 is provided at intervals of a predetermined distance, e.g., one centimeter, with gradations 38 of any suitable measure, e.g., microliters. The gradations 38 are marked as a plurality of rings about the distal end, and may be slightly indented into the outer surface thereof. Alternatively, the gradations 38 may be of a distinctive color to allow the operator to precisely aspirate an exact quantity of a fluid medium to achieve a consistent protocol. As best shown in FIGS. 2-5, the remote distal tip 46 of the inner lumen 36 is provided with a smoothly radiused chamfer for minimal trauma to the uterine tissues. The inner lumen 36 in accordance with this embodiment of the invention is preferably soft and flexible and formed of a biologically acceptable synthetic polymer.

Referring now to FIGS. 1-4, there is shown a standard syringe 52 having a barrel 56 and a plunger 60 disposed therein. Referring now to FIG. 1, the syringe 52 is shown with the plunger 60 disposed fully within the length of the barrel 56. The syringe 52 includes a distal end 61 which is sized to snugly fit within the inner bore 42 of the inner lumen 36.

Referring now to FIGS. 2-4, to load the inner lumen 36 for the embryo transfer procedure, the distal end 61 of the syringe 52 is inserted into the inner bore 42 of the inner lumen 36 with the plunger 60 disposed fully within the length of the barrel 56 of the syringe 52. A predetermined amount of a first fluid medium, e.g., from 6 to 9 microliters of a wash fluid 64, is drawn into the internal passageway 34 of the inner lumen 36 and into the barrel 56 of the syringe 52 by withdrawing the plunger 60 along a portion of the length of the barrel 56. Next, an excess amount of the wash fluid 64 is ejected from the syringe 52 and internal passageway 34 by depressing the plunger 60. By utilizing the gradations 38 marked on the distal end of the inner lumen 36, an accurate volume of wash fluid 64 can be obtained within the internal passageway 34. The ET delivery catheter 6 is then held vertically to enable air to escape out the remote distal tip 46 of the inner lumen 36. Often, the sides of the ET delivery catheter 6 are tapped by the forefingers to loosen any air bubbles from the internal sides of the barrel 56.

Referring now to FIG. 3, a predetermined amount of a second fluid medium, e.g., approximately 3 microliters of a separation oil 68, may be drawn into the internal passageway 34 of the inner lumen 36 adjacent the first fluid medium, by slowly withdrawing the plunger 60 from the barrel 56 of the syringe 52, as indicated by the arrow in FIG. 3. Any suitable separation oil 68 may be utilized for the purpose of separating the wash fluid 64 from the culture medium containing one or more embryos 72. One particular product which could be utilized as a separation oil in accordance with the present invention is an enhanced oil for tissue culture manufactured by Conception Technologies of San Diego, Calif. under catalog numbers OTC-100 (100 mL) and OTC-500 (500 mL). By utilizing the gradations 38 marked on the distal end of the inner lumen 36, an accurate volume of the separation oil 68 within the internal passageway 34 can be achieved. Likewise, unwanted air and any unneeded volume of separation oil 68 can be expelled through the remote distal tip 46 by depressing the plunger 60 of the syringe 52 and/or tapping with forefingers to loosen air bubbles.

Lastly, as best shown in FIG. 4, the gradations 38 located at the distal end of the inner lumen 36 enable an operator to draw a predetermined amount of a third fluid medium, e.g., approximately 3-6 microliters of a fluid culture medium containing one or more embryos 72, into the internal passageway 34 of the inner lumen 36. As shown in FIG. 4, the third fluid medium in which the embryos 72 are located is shown as being situated adjacent the separation oil 68. The fluid culture medium in which the embryos 72 are located includes a water-based portion and sometimes, an oil-based portion. When an oil-based portion is used, it is done so to prevent evaporation of the water-based portion and prevent dehydration of the embryos 72. One product which is suitable for utilizing as the oil-based portion of the fluid culture medium is the enhanced oil for tissue culture manufactured by Conception Technologies of San Diego, Calif. under catalog numbers OTC-100 (100 mL) and OTC-500 (500 mL), as mentioned in connection with the separation oil described above.

As best shown in FIG. 4, the three fluid media, e.g., the wash fluid 64, the separation oil 68, and the plurality of embryos 72 disposed within a fluid culture medium are shown disposed within the internal passageway 34 of the inner lumen 36. The separation oil 68 is utilized as a replacement to the volume of air which under existing techniques is utilized to separate the wash fluid 64 from the embryos 72. By replacing the volume of air with the separation oil 68, the drawbacks associated with the use of air in embryo transfer procedures is eliminated. For example, the use of a separation oil 68 will facilitate movement of the embryos 72 from the site of ejection to the optimal location for implantation within the uterus and will facilitate interaction between the embryo 72 and the receptive surface of the uterus. Embryos 72 will flow more readily within a liquid environment than a gaseous (air) environment.

In accordance with the present invention, ingredients may be added to the separation oil 68 and/or wash fluid 64, including progesterone and/or estrogen to stimulate the luteal phase which determines the time of ovulation within the menstrual cycle and establishes the peak moment of receptivity within the uterus. By including such hormones within the separation oil 68 and wash fluid 64 for administration into the uterus, the concentrations of such hormones needed for luteal stimulation and support is substantially less than required when such hormones are administered by vaginal suppository, intramuscular or other systemic means.

It should be understood that the hormones needed for stimulation of the luteal phase may be added to the separation oil 68 and/or the wash fluid 64 and delivered directly into the uterus during an ET procedure utilizing the delivery catheter 6 described herein. Alternatively, the hormones may be introduced directly into the uterus utilizing any other suitable delivery device and may be delivered into the uterus at any point in time, either prior to or during the ET procedure.

One embodiment of the present invention is a method to hormonally prepare the uterus prior to the introduction of a fertilized egg during embryonic implantation. Embryonic Implantation in humans is a complex process, part of which requires hormonal preparation of the uterus prior to the involvement of a fertilized egg. This preparation has been described in general terms as "the window of implantation" of the ovulation cycle whereby progesterone is secreted by the corpus luteum, situated on the developing ovary, and travels down the fallopian tube into the uterus in a slow but timely manner each month of a woman's hormonal cycle. Consequently, embryonic implantation is a synchronized process between hormonal preparation and implantation of a fertilized egg.

Generally about 15% of the population experience difficulty in achieving pregnancy by the natural process involving hormonal preparation and implantation so many revert to an assisted or artificial means of achieving pregnancy such as in vitro fertilization. For in vitro fertilization to occur, the same uterine hormonal preparation during the window of implantation, as in a natural pregnancy, must be achieved in order for successful implantation of a deposited embryo and ultimate pregnancy.

Current approaches to methods involving uterine preparation include intramuscular injection (IM) of micronized progesterone in oil and peri-vaginal delivery (PV) of an assortment of products that contain micronized progesterone such as: gels, effervescent tablets, creams, suppositories, etc. These forms of hormonal delivery enter the bloodstream and the progesterone molecules eventually reach the outside of the uterus (myometrium) and propagate toward the endometrial innermost layer of the uterus, where implantation occurs.

Unfortunately, these conventional "extra-uterine" systemic administrations of progesterone result in inconsistent bioavailability, especially with respect to timing and the window of implantation which affects proper and consistent embryonic implantation. Evidence supported by endometrial biopsies demonstrate periods of time when progesterone concentrations are far below the levels known to facilitate implantation. Conversely, some endometrial biopsies show excessively high progesterone concentration levels, far outside the norm, which act as a deterrent to implantation, much like an intrauterine device (IUD) that emits daily high doses of progesterone to prohibit implantation and pregnancy.

One embodiment of the present invention provides a means to control the bioavailability of progesterone within an acceptable concentration and time range in order to establish a progesterone dominant uterus (over antagonist-estrogen) and achieve implantation (and ultimately pregnancy) more often than the 27% fertility plateau that is witnessed in IVF when one single embryo is transferred to the uterus, Another embodiment of the invention provides a method of targeted intrauterine administration to precisely establish a progesterone dominant uterus within the window of implantation, resulting in a uterus primed and ready to receive a developing blastocyst for implantation. This targeted approach mitigates the anatomical and physiological aspects found in prior methods that restrict progesterone reaching the endometrium, while eliminating the excessive buildup that occurs which hinders implantation via conventional methods.

Accordingly, a hormonal preparation containing a formulation with at least one implantation promoter such as progesterone, estrogen or combinations thereof is delivered to the target site. The hormonal preparation is administered in the proper proportions and with the proper timing to optimize and ensure the probability of a successful pregnancy. The time period for administration of a hormonal preparation prior to depositing the embryo varies from the same day to 270 days post administration. The concentration range of the implantation promoter is between approximately 0.001 micrograms to 1000 milligrams. Hormonal preparations may be in a nanoformulation and incorporate a micronized particle mix using micronization methods known in the art such as wet-milling of particles. Excipients can be used which are known to alter the pharmacokinetics and dynamics of hormonal bioavailability.

The optimum specific time period and hormone concentration range can be determined through routine experimentation wherein the most desirable bioavailability range for promoting the maximum effect of uterine factors necessary for implantation is determined. Because of the direct delivery to the endometrial surface at precisely the right time, timing and concentration can be easily modified for optimum activity of the uterine factors. These factors include; Aquaporins (AQPs), Epithelial Sodium Channels (ENaCs), Prostaglandins, Activation of the Sodium Pump and HNE-1 Protein for embryonic transport and immobilization, and other genomic factors on the uterine and blastocyst surfaces that require precise hormonal exposure to assure needed dialog between the uterus and blastocyst (termed: maternal dialog), for the continued decidualization process of implantation to occur.

A still further embodiment of the present invention is where the administration of an implantation promoter to the uterine target site occurs simultaneously with the deposition of the embryo. Administration and deposition occur simultaneously through the same delivery device.

Depositing the fertilized embryo at the implantation site can occur through any delivery means know in the art. These may include an embryo transfer catheter, syringe, or other ejection device. The fertilized embryo can also be deposited directly by manually placement of the embryo.

However another embodiment of the present invention incorporates the use of a delivery means having a catheter with an outer sheath and an inner lumen slidably disposed within the outer sheath, as described elsewhere herein, the internal lumen has an internal passageway configured to hold an embryo and having a means for quantitative administration of a fluid medium. Accordingly both the embryo and hormonal preparation can be delivered through the same device with the quantitative administration of a fluid medium containing a hormonal preparation having a formulation with at least one implantation promoter. This delivery means is ideally suited for the simultaneous delivery of a hormone preparation and the deposition of the fertilized embryo. Also because of the quantitative delivery of the device, deposition of the fertilized embryo can occur with the precisely-timed delivery of a prior amount of implantation promoter to have the uterus hormonally prepared for implantation.

Figure 7:
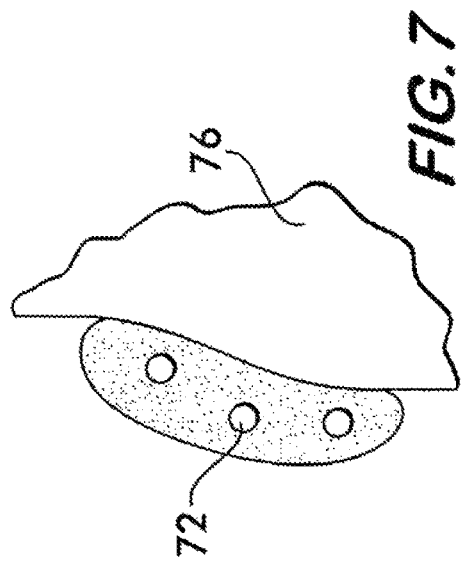
FIG. 7 is an illustration of several embryos implanted on the wall of a uterus after an embryo transfer procedure has been conducted.

Referring now to FIGS. 5 and 7, once the predetermined volumes of fluid media have been accurately drawn within the internal passageway 34 of the inner lumen 36, delivery of the embryos 72 to the uterus 76 is possible. The distal ends of the outer sheath 10 and inner lumen 36 are brought together. The physician and/or embryologist directs the end of the ET delivery catheter 6 transvaginally to the desired location within the uterus, either by conventional means or by improved ultrasound guided techniques. The gradations 28 provided at the distal end of the outer sheath 10 enable the physician and/or the embryologist to determine the distance the catheter 6 has been inserted into the uterus. The ET delivery catheter 6 must be gently advanced through the cervical canal to overcome obstruction or tortuous route so that the delivery catheter 6 can pass into the uterus.

The physician and/or embryologist then ejects the embryos 72 through the distal end of the inner lumen 36 by depressing the plunger 60 of the syringe 52. In this manner, the entire contents are expelled out of the internal passageway 34. In this manner, the wash fluid 64 washes the wall of the internal passageway 34 and carries out any adherent embryos 72 that may have attached themselves to the wall of the internal passageway 34 by way of surface tension. Once the embryo transfer is completed, the physician extracts the distal tip of the ET delivery catheter from the cervix. This method of ET is superior to other methods because the delivered embryos are much more likely to flow within a liquid environment than a gaseous (air) environment.

The details of the construction or composition of the various elements of the ET delivery catheter 6 of the present invention not otherwise disclosed are not believed to be critical to the achievement of the advantages of the present invention, so long as the elements possess the strength or flexibility or softness needed for them to perform as disclosed. The details of such construction is believed to be well within the ability of one of ordinary skill in this area, in view of the present disclosure, and are within the spirit of the invention and the scope of the claims.

The invention claimed is:

1. A method for artificial embryonic implantation in a uterine wall of a female subject comprising:
   a. directly administering at least one implantation promoter in a nanoformulation sufficient to promote an activation of uterine factors at a target site on the uterine wall within a window of implantation; and
   b. depositing a fertilized embryo at a prepared site
   wherein administering the implantation promoter and depositing a fertilized embryo are through a distal end of an inner lumen for an embryo transfer delivery catheter to locally target a portion of the uterine wall.

2. The method of claim 1 wherein the female subject is human.

3. The method of claim 1 wherein the implantation promoter is selected from a group consisting of known amounts of progesterone, estrogen, and a combination thereof.

4. The method of claim 1 wherein the implantation promoter is progesterone.

5. The method of claim 1 wherein a concentration of the implantation promoter is between approximately 0.001 micrograms to 1000 milligrams administered at the target site.

6. The method of claim 1 wherein the uterine factors are selected from the group consisting of aquaporins, epithelial sodium channels, prostaglandins, activation of a sodium pump, HNE-1 protein and combinations thereof.

7. The method of claim 1 wherein the window of implantation is a time period for having a maximum effect on the uterine factors as determined at the target site for an individual female subject.

8. The method of claim 1 wherein the window of implantation is between approximately a day of depositing a fertilized embryo to approximately 270 days prior to depositing a fertilized embryo.

9. The method of claim 1 wherein administering the implantation promoter through the embryo transfer delivery catheter is prior to the delivery of the fertilized embryo.

* * * * *